United States Patent [19]

Gearhart et al.

[11] Patent Number: 6,090,622
[45] Date of Patent: Jul. 18, 2000

[54] HUMAN EMBRYONIC PLURIPOTENT GERM CELLS

[75] Inventors: John D. Gearhart; Michael Joseph Shamblott, both of Baltimore, Md.

[73] Assignee: The Johns Hopkins School of Medicine, Baltimore, Md.

[21] Appl. No.: 08/829,372

[22] Filed: Mar. 31, 1997

[51] Int. Cl.$^7$ ............................ C12N 5/08; C12N 5/00
[52] U.S. Cl. ................. 435/366; 435/325; 424/93.21
[58] Field of Search ................. 424/93.1, 9.1, 424/93.21; 435/172.3, 325, 352, 353, 366

[56] References Cited

U.S. PATENT DOCUMENTS

| | | | |
|---|---|---|---|
| 5,035,994 | 7/1991 | Civin | 435/2 |
| 5,061,620 | 10/1991 | Tsukamoto et al. | 435/7.21 |
| 5,096,822 | 3/1992 | Rosenkrans, Jr. et al. | 438/388 |
| 5,166,065 | 11/1992 | Williams et al. | 435/377 |
| 5,196,315 | 3/1993 | Ronnett et al. | 435/29 |
| 5,437,994 | 8/1995 | Emerson et al. | 435/373 |
| 5,453,357 | 9/1995 | Hogan | 435/7.21 |
| 5,523,226 | 6/1996 | Wheeler | 435/325 |
| 5,589,376 | 12/1996 | Anderson et al. | 435/325 |
| 5,591,625 | 1/1997 | Gerson et al. | 435/366 |
| 5,654,183 | 8/1997 | Anderson et al. | 435/172.3 |
| 5,670,351 | 9/1997 | Emerson et al. | 435/172.3 |
| 5,670,372 | 9/1997 | Hogan | 435/240.2 |
| 5,672,499 | 9/1997 | Anderson et al. | 435/69.1 |
| 5,690,926 | 11/1997 | Hogan | 424/93.1 |
| 5,750,397 | 5/1998 | Tsukamoto et al. | 435/372 |
| 5,811,094 | 9/1998 | Caplan et al. | 424/93.7 |
| 5,814,440 | 9/1998 | Hill et al. | 435/2 |
| 5,824,489 | 10/1998 | Anderson et al. | 435/7.21 |
| 5,843,780 | 12/1998 | Thompson | 435/363 |

FOREIGN PATENT DOCUMENTS

| | | |
|---|---|---|
| 90/03432 A1 | 4/1990 | WIPO. |
| 95-10599 | 4/1995 | WIPO. |
| 97/20035 | 6/1997 | WIPO. |
| 97/25412 | 7/1997 | WIPO. |
| 97/25413 | 7/1997 | WIPO. |

OTHER PUBLICATIONS

Fourcin M, et al. gp130 transducing receptor cross–linking is sufficient to induce interleukin–6 type responses. J. Biol. Chem. May 17, 1996;271(20):11756–60.

Wijdenes J, et al. Interleukin–6 signal transducer gp130 has specific binding sites for different cytokines as determined by antagonistic and agonistic anti–gp130 monoclonal antibodies. Eur. J. Immunol. Dec. 1995;25(12):3474–81.

Koshimizu et al., "Functional requirement of gp130–mediated signaling for growth and survival of mouse primordial germ cells in vitro and derivation of embryonic germ (EG) cells," (1996), *Development* 122:1235–1242.

R. Ian Freshney, "Culture of Animal Cells: A manual of Basic Technique," Second Edition, Chapter 10, 1987, Alan R. Liss, Inc., New York, NY.

Davis et al., "LIFR Beta and gp130 as heterodimerizing signal transducers of the tripartite CNTF receptor," (Jun. 18, 193), *Science* 260(5115): 1805–8.

Taga T., "Gp130, a shared signal transducing receptor component for hematopoietic and neuropoietic cytokins," Jul. 1996, *J. Neurochem* 67(1):1–10.

Resnick et al., "Long–term proliferation of mouse promordial germ cells in culture," Oct. 8, 1992, *Nature*, vol. 359, 550–551.

Donovan et al., "Primoridal germ cells, stem cells and testicular cancer," 1998, *APMIS* 106:134–141.

Uchida et al., "Effects of Feeder Cells and Growth Factors of the Proliferation of Mouse Primordial Germ Cells," Jan. 1995, *Theriogenology* 44:9–16.

Olie et al., "Heterogeneity in the in vitro survival of proliferation of human seminoma cells," 1995, *British Journal of Cancer* 71, 13–17.

Matsui et al., "Derivaiton of Pluripotential Embryonic Stem Cells from Murine Primordial Germ Cells in Culture," Sep. 4, 1992, *Cell*, vol. 70, 841–847.

Labosky et al., "Mouse embryonic germ (EG) cell lines: transmission through the germline and differences in the methylation imprint of insulin–like growth factor 2 receptor (Igr2r) gene compared with embryonic stem (ES) cell lines," 1994, *Development* 120, 3197–3204.

Ohkubo et al., "Autonomous Regulation of Proliferation and Growth Arrest in Mouse Primordial Germ Cells Studied by Mixed and Clonal Cultures," 1996, *Experimental Cell Research* 22, 291–297.

Labosky et al., "Embryonic germ cell lines and their derivation from mouse primordial germ cells," 1994, *Germline development*, Wiley, Chichester (Ciba Foundation Symposium 182), 157–178.

Moore, "Characterization of porcine inner cell mass(pICM) and primordial germ cells (pPGC) for the development of transgenic embryonic cell lines," May 1998, *Dissertation Abstracts International*, vol. 58, No. 11.

Durcova–Hills et al., "Short–term Culture of Porcine Primordial Germ Cells," 1998, *Theriogenology*, vol. 49, No. 1, p. 237.

Smith et al., "Buffalo Rat Liver Cells Produce a Diffusible Activity Which Inhibits the Differentiation of Murine Embryonal Carcinoma and Embryonic Stem Cells," 1987, *Development Biology* 121, 1–9.

Taylor et al., "Human Stem Cell Factor Promoter Deoxyribonucleic Acid Sequence and Regulation by Cyclic 3', 5'–Adenosine Monophosphate in a Sertoli Cell Line," Dec. 1996, *Endocrinology*, 137, No. 12, 5407–5414.

Jiang et al., "Cloning and characterization of the 5' flanking region of the stem cell factor gene in rat Sertoli cells," Jan. 31, 1997, *Gene* 185, No. 1, 285–290.

(List continued on next page.)

*Primary Examiner*—Jon P. Weber
*Attorney, Agent, or Firm*—Fish & Richardson P.C.

[57] ABSTRACT

Primordial germ cells extracted from post blastocyst human embryos, such as from the gonadal ridges of a 8–11 week LMP human embryo, are disclosed. The primordial germ cells are cultured in long term culture (more than 30 days) resulting in cells that resemble embryonic stem cells in morphology and pluripotency. The cells are maintained several months in culture and can be genetically manipulated using transgenic technology to insert heterologous genetic material.

15 Claims, 3 Drawing Sheets

OTHER PUBLICATIONS

De Felici et al., "Growth Factors in Mouse Primordial Germ Cell Migration and Proliferation," 1994, *Progress in Growth Factor Research* 5: 135–143.

Cheng et al., "Role of Leukemia Inhibitory Factor and its Receptor in Mouse Primordial Germ Cell Growth," 1994, *Development* 120, 3145–3153.

Smith, "Culture and Differentiation of Embryonic Stem Cells," 1991, *J. Tissue Culture Method* 13:89–94.

Evans et al., "Derivation and Preliminary Characterization of Pluripotent Cell Lines from Porcine and Bovine Blastocysts", *Theriogenology*, Jan. 1990, vol. 33, No. 1, pp. 125–128.

Beardsley, "In Focus: Culturing New Life," *Scientific American*, 11 (Jun. 1998).

Lewis, "Embryonic Stem Cells Debut Amid Little Media Attention," *The Scientist*, 1 (Sep. 29, 1997).

Thomson et al. (1995) Proc. Nat. Acad. Sci. U.S.A., 92(17), "Isolation of a Primate Embryonic Stem Cell Line", pp. 7844–7848.

HUMAN EMBRYONIC PLURIPOTENT GERM CELLS

BACKGROUND OF THE INVENTION

1. Field of the Invention

This invention relates generally to the field of in vitro culture of undifferentiated cells and methods of producing such cells. More specifically, the invention relates to methods and compositions for production of human pluripotent embryonic germ cells or (hEG) cell lines.

2. Description of Related Art

Pluripotent embryonic stem cells are derived principally from two embryonic sources. In the mouse, one type of pluripotent stem cell can be isolated from cells of the inner cell mass of a pre-implantation embryo and are termed embryonic stem (ES) cells (Evans and Kaufman, *Nature* 292: 154–156, 1981). A second type of mouse pluripotent stem cell can be isolated from primordial germ cells [PGCs] located in the genital ridges of day 8.5 post coitum mouse embryos and has been termed an embryonic germ cell (EG) (Matsui et al., *Nature* 353: 750–751, 1991; Resnick et al., *Nature* 359: 550–551, 1992; Hogan, U.S. Pat. No. , 5,453, 357). Both types of cells are pluripotent and demonstrate germline genetic transmission in the mouse.

The extent of pluripotency in pluripotent cell cultures is generally determined experimentally. For example, one method utilizes measuring the high intracellular levels of the enzyme alkaline phosphatase found in ES, PGCs, and EGs. Demonstration of intracellular alkaline phosphatase by histological staining was historically used to define and locate PGCs (Chiquoine, *Anat. Rec.* 118: 135–146, 1954). Such staining remains one of the criteria for the definition of new pluripotent cell cultures. ES and EGs propagated in vitro can contribute efficiently to the formation of chimeras, including germline chimeras, but in addition, both of these cell types can be genetically manipulated in vitro without losing their capacity to generate germ-line chimeras.

ES and EGs are useful in methods for the generation of transgenic animals. Such methods have a number of advantages as compared with more conventional techniques for introducing new genetic material into such animals, such as zygote injection and viral infection. First, the gene of interest can be introduced and its integration and expression characterized in vitro. Second, the effect of the introduced gene on the ES or EG growth can be studied in vitro. Third, the characterized ES or EGs having a novel introduced gene can be efficiently introduced into embryos by blastocyst injection or embryo aggregation and the consequences of the introduced gene on the development of the resulting transgenic chimeras monitored during prenatal or postnatal life. Fourth, the site in the ES or EG genome at which the introduced gene integrates can be specified, permitting subsequent gene targeting and gene replacement (Thomas, K. R. and Capecci, M. R. *Cell* 51: 503–512, 1987).

However, it is known that EGs or ES cells and certain EC (embryonal carcinoma) cell lines will only retain the stem cell phenotype in vitro when cultured on a feeder layer of fibroblasts (such as murine STO cells, e.g., Martin, G. R. and Evans, M. J. *Proc. Natl. Acad. Sci. USA* 72: 1441–1445, 1975) when cultured in medium conditioned by certain cells (e.g. Koopman, P. And Cotton, R. G. H. *Exp. Cell* 154: 233–242, 1984; Smith, A. G. and Hooper, M. L. *Devel. Biol.* 121: 1–91, 1987) or by the exogenous addition of leukemia inhibitory factor (LIF). Such cells can be grown relatively indefinitely using the appropriate culture conditions. They can be induced to differentiate in vitro using retinoic acid or spontaneously by removal of the feeder layer conditioned media or exogenous LIF. In addition, these cells can be injected into a mouse blastocyst to form a somatic and germ line chimera. This latter property has allowed mouse ES cells to be used for the production of transgenic mice with specific changes to the genome. See M. Evans et al., *Nature* 292: 154 (1981); G. Martin, *Proc. Natl. Acad. Sci. USA* 78: 7638 (1981); A. Smith et al., *Developmental Biology* 121: 1 (1987); T. Doetschman et al., *Developmental Biology* 127: 224 (1988); A. Handyside et al., *Roux's Arch Dev. Biol.* 198: 48 (1989).

In the absence of feeder cells or conditioned medium, ES or EGs spontaneously differentiate into a wide variety of cell types, resembling those found during embryogenesis and in the adult animal. With the appropriate combinations of growth and differentiation factors, mouse ES and EGs generate cells of the hematopoietic lineage in vitro (Keller, G., et al., *Mol. Cell. Biol.* 13: 473–486, 1993; Palacios, R., E. Golunski, and J. Samaridis, *Proc. Natl. Acad. Sci. USA* 92: 7530–7534, 1995; Rich, T., *Blood* 86: 463–472, 1995). Additionally, mouse ES cells have been used to generate in vitro cultures of neurons (Bain, G., et al., *Developmental Biology* 168: 342–357, 1995; Fraichard, A., et al., *J. Cell Science* 108: 3161–3188, 1995), cardiomyocytes (heart muscle cells) (Klug, M., M. Soonpaa, and L. Field, *Am. J. Physiol.* 269: H1913-H1921, 1995), skeletal muscle cells (Rohwedel, J., et al., *Dev. Biol.* 164: 87–101, 1994), and vascular cells (Wang, R., R. Clark and V. Bautch, *Development* 114: 303–316, 1992). The factors responsible for maintaining the pluripotency of ES and EGs remain poorly characterized and are often dependent upon the species from which the cells have been harvested.

Subsequent to the work with mouse embryos, several groups have attempted to develop stem cell lines from sheep, pig, and cow. A cell line with embryonic stem cell-like appearance has reportedly been cultured from porcine embryos using culture conditions similar to mouse (M. Evans et al., PCT Application WO90/03432; E. Notarianni et al., *J. Reprod. Fert., Suppl.* 41: 51, 1990; J. Piedrahita et al., *Theriogenology* 34: 879, 1990; E. Notarianni et al., *Proceedings of the* 4th World Congress on Genetics Applied to Livestock Productions, 58, Edinburgh, July 1990). Other groups have developed avian stem cell lines from chickens (Pain et al., *Dev.* 122:1996).

To date, there have been no reports for the establishment of human EG cells or cell lines. Any method which would allow production of human ES and EG would be desirable since, human EG cell lines would permit easier study of early human development, and the use of such human EG cell lines would enable the development of cell cultures for transplantation and manufacture of bio-pharmaceutical products.

SUMMARY OF THE INVENTION

The present invention provides a human embryonic pluripotent germ cell (hEG) line and a method of producing cells exhibiting an hEG phenotype. hEGs are derived from EGs isolated from gonadal tissues, genital ridges, mesenteries or embryonic yolk sacs of human embryos and cultured under conditions which allow long term cell culture (more than 30 days). The resulting hEG cells resemble ES cells in morphology, biochemical histotype and in pluripotency. These cells can be passaged in culture, maintained for several months in culture, and survive cryopreservation.

An object of the invention is to provide a method for producing human cell lines which exhibit an ES cell-like phenotype. Another object of this invention is intended to provide human pluripotential embryonic germ cell (hEG) lines in general, as well as differentiated cell lines derived from hEGs. Another object is to provide human transgenic cells, cell lines, or tissues using the hEGs of the invention. Another object is to provide hEG cells or hEG derived stem cells of restricted developmental lineage for transplantation. Yet another object is to provide useful pharmaceutical products from the cells or cell lines of the present invention.

An advantage of the invention is that large numbers of hEG cells can be quickly and efficiently produced. In one embodiment of the invention, the starting material are primordial germ cells isolated over a period of 3–13 weeks post fertilization, from human fetal/embryonic yolk sac, mesenteries, and gonadal ridges, successively. In still another embodiment, gonocytes of later testicular stages are isolated.

BRIEF DESCRIPTION OF THE DRAWINGS

FIG. 1 shows phase contrast microscopy photographs of human embryonic germ cells (hEGs) showing positive histological staining for alkaline phosphatase.

FIG. 2 shows phase contrast microscopy photographs of human embryonic germ cell colonies.

DETAILED DESCRIPTION OF THE INVENTION

Figure 1A:
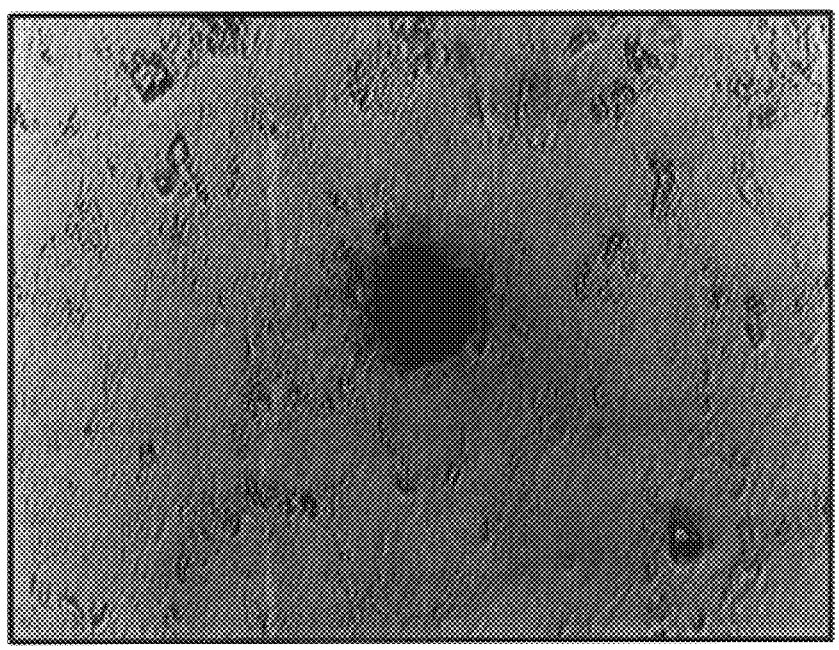
FIG. 1a shows a non-motile PGC with characteristic rounded morphology.
Figure 1B:
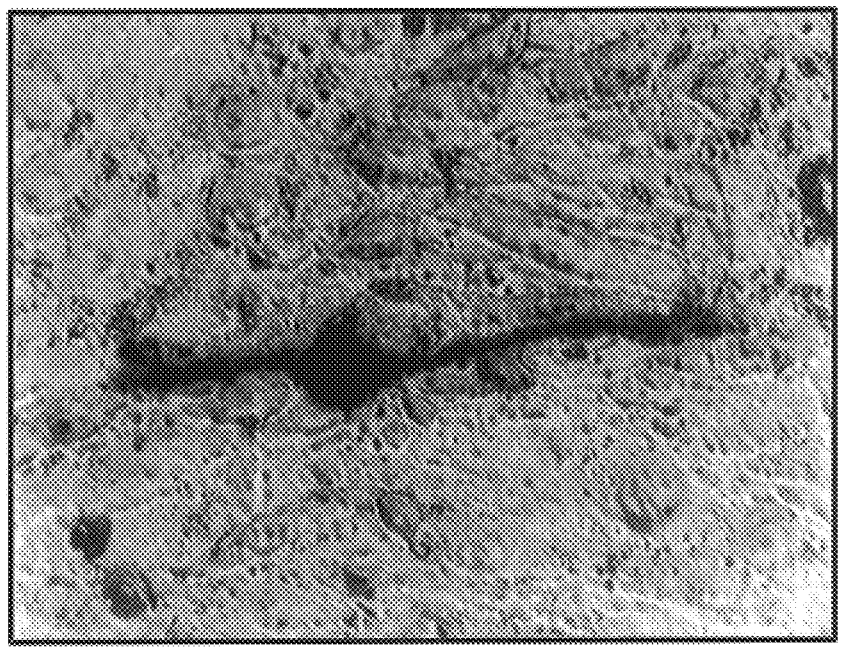
FIG. 1b shows a migratory PGC with characteristic psuedopodal morphology.
Figure 2A:
FIG. 2a demonstrates a morphology characteristic of a multilayer EG colony.
Figure 2B:
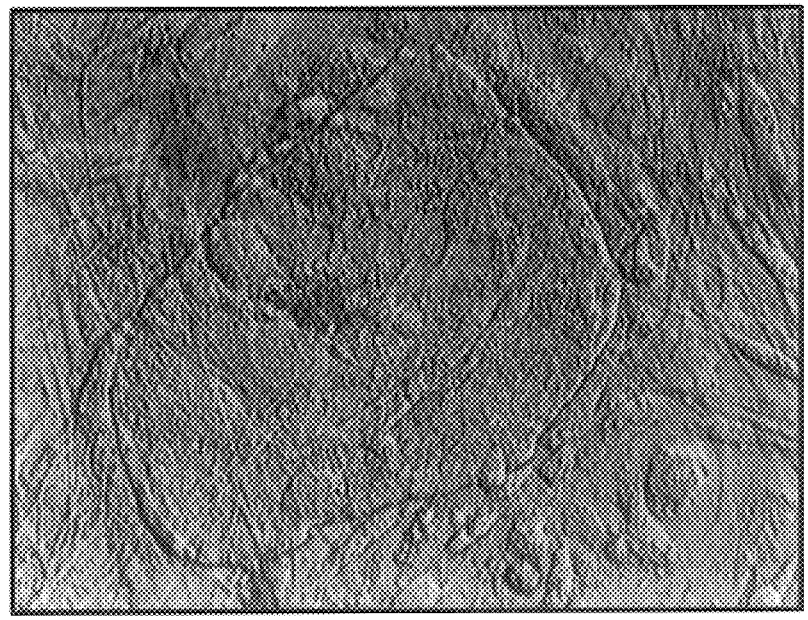
FIG. 2b demonstrates a morphology characteristic of a monolayer EG colony.
Figure 3A:
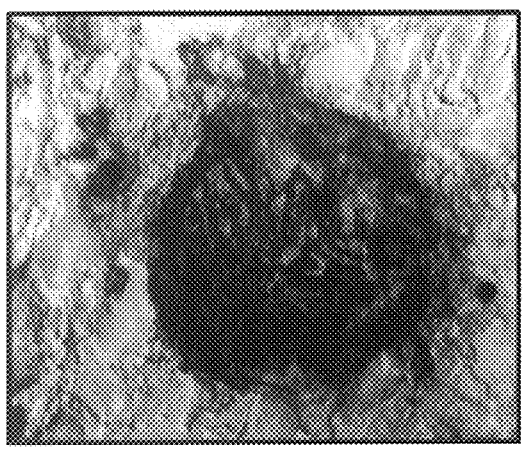
FIG. 3 shows phase contrast microscopy photographs of human embryonic germ cell (hEG) colonies showing positive immunohistochemical staining for: (A) stage specific embryonic antigen-1 (SSEA-1); (B) stage specific embryonic antigen-3 (SSEA-3); (C) stage specific embryonic antigen-4 (SSEA-4); (D) a cell surface antigen that binds with the antibody having the binding specificity of the monoclonal antibody designated TRA-1-60; (E) a cell surface antigen that binds with the antibody having the binding specificity of the monoclonal antibody designated TRA-1-81; (F) alkaline phosphatase activity.
Figure 3B:
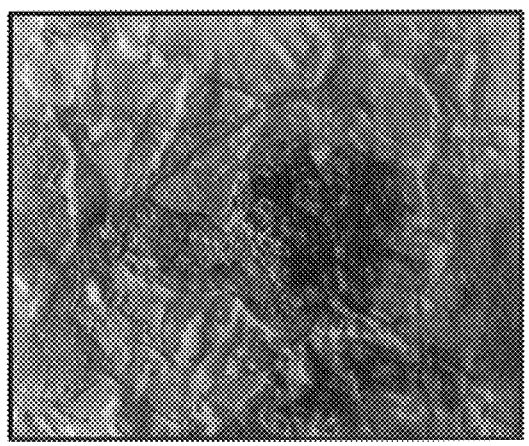
Figure 3C:
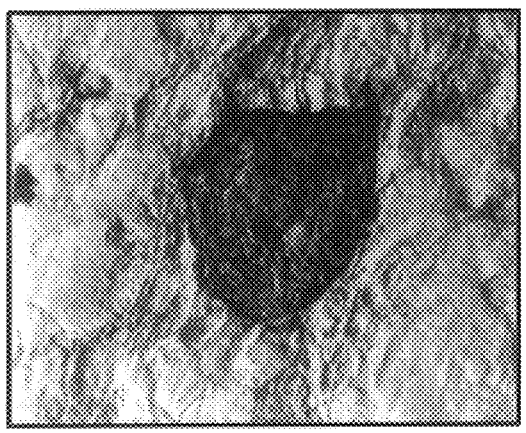
Figure 3D:
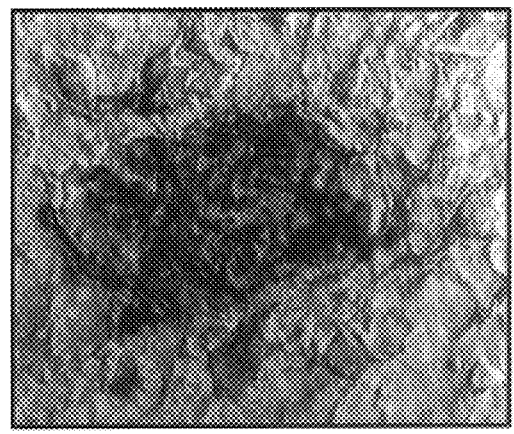
Figure 3E:
Figure 3F:
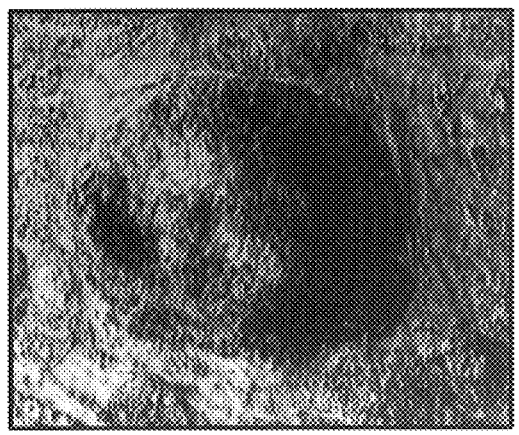

Before the present human cells expressing an embryonic pluripotent phenotype, compositions, reagents and methods and uses thereof are described, it is to be understood that this invention is not limited to the cells, compositions, reagents, methods or uses described, as such cells, compositions, reagents, methods or uses may, of course, vary. It is also to be understood that the terminology used herein is for the purpose of describing particular embodiments only, and that the terminology used herein is not intended to limit the scope of the present invention which will only be limited by the appended claims.

It must be noted that as used herein and in the appended claims, the singular forms "a," "an," and "the," include plural referents unless the context clearly indicates otherwise. Thus, for example, reference to "a cell" includes one or more of such cells or a cell line derived from such a cell, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

In one embodiment, the invention provides a method of producing pluripotent human cells exhibiting an embryonic cell phenotype. The starting material is primordial germ cells isolated over a period of 3–13 weeks post-fertilization, from embryonic yolk sac, mesenteries, or gonadal ridges, successively from human embryos/fetus. In another embodiment, gonocytes of later testicular stages are isolated. The primordial germ cells (PGCs) are cultured on mitotically inactivated STO cells under particular conditions in long term cell culture (more than 30 days) to allow the production of hEGs. The resulting cells resemble human ES cells in morphology and in biochemical histotype. The cells can be passed several times in culture, maintained for several months in culture and survive cryopreservation.

Specifically, the present invention describes two human pluripotential embryonic germ cell (hEG) cultures, designated HEG-KH and hEG-GU. The HEG-KH and HEG-GU cell cultures are derived from the gonadal anlagen or genital ridges of approximately 8 and 11-week last menstrual period (LMP) aborted human fetal material, respectively. Considering the source and colony morphology of these cells, they most resemble or are human pluripotent embryonic germ cells (hEGs).

Human pluripotential stem cells (hEG) are human cells that can be cultured indefinitely in an undifferentiated state, yet retain the ability to be differentiated into a variety of cell and tissue types. In accordance with the present invention, the terms "pluripotent" and "pluripotential cells" refer to those cells which retain the developmental potential to differentiate into a wide range of cell lineages including the germ line. The terms "embryonic stem cell phenotype" and "embryonic stem-like cell" also are used interchangeably herein to describe cells which are undifferentiated and thus are pluripotent cells and which are visually distinguished from other adult cells of the same animal.

The ability of hEG cells to differentiate in vitro into a wide variety of cell types including the ability to differentiate into embryonic and more highly differentiated cell types which can easily be tested by means common to those in the art. For example, to induce differentiation in monolayer cultures hEG cells are cultured for 2 weeks without passage onto a fresh STO feeder layer. To induce differentiation in suspension culture, the cells are passed onto a gelatinized plate to eliminate possible contamination by fibroblasts. After 4 to 7 days in culture, colonies are gently dislodged from the plate by mouth pipette and disaggregated after incubation in 0.25% trypsin-EDTA for 10–15 min. Dissociated cells are cultured in a microdrop of hEG culture medium containing 0.3 µM retinoic acid (Sigma) on a 35-mm nonadhesive petridish (Falcon). Suspension cultures are monitored daily for embryoid body formation which is indicative of a differentiated phenotype. (Similar experiments testing for differentiation of attached hEG cells are well known to those in the art.) Cell culture media is changed every other day. Based on the resulting differentiated morphological types putative hEG cells can be tested for their pluripotency.

The term "primordial germ cells" is used to describe undifferentiated embryonic germ cells isolated over a period of post fertilization from the anlagen or from yolk sac, mesenteries, gonadal ridges, successively of human embryos/fetus. In another embodiment, gonocytes of later testicular stages are isolated. The resulting hEG cells resemble ES cells in morphology, biochemical histotype and in pluripotency. These cells can be passaged in culture, maintained for several months in culture, and survive cryopreservation. By the term "anlagen" is meant the rudiment or the primordia of an organ, tissue or part thereof. The term "cell" as used herein also refers to individual cells, cell lines, or cultures derived from such cells. The term "embryonic germ cell" is used to describe cells of the present invention that exhibit an embryonic pluripotent cell phenotype. The term "cell line" as used herein refers to hEG cells or cells derived therefrom such as are maintained in vitro culture. A cell line is substantially free of other cells.

The terms "human embryonic germ cell (hEG)" or "embryonic germ cell" can be used interchangeably herein to describe human cells, or cell lines thereof, of the present invention that exhibit a pluripotent embryonic stem cell phenotype that have particular characteristics. For example, in one embodiment, the hEG is pluripotent and is characterized by the presence of markers associated with specific epitopic sites identified by the binding of particular antibodies and the absence of certain markers as identified by the lack of binding of certain antibodies. In another embodiment, the hEG is dependent on some growth factors for maintenance in the cultured state. Growth factors, as defined herein, are intercellular signaling polypeptides which control both the development and maintenance of cells, and the form and function of tissues. Preferably, the growth factor used in the method of the present invention is basic growth factor (bFGF). In another embodiment, the hEG requires a ligand which binds to a receptor on hEG that can heterodimerize with glycoprotein 130 (gp130). The ligand is oncostatin-M or leukemia inhibitory factor (LIF). In another embodiment, the hEG stains positively for the presence of alkaline phosphatase. In another embodiment, the hEG expresses cell surface antigens SSEA-1 and SSEA-4. In another embodiment, the hEG expresses cell surface antigens that bind with antibodies having the binding specificity of monoclonal antibodies TRA-1-60 and TRA-1-8 1. By "binding specificity" is meant that the present invention contemplates all monoclonal antibodies that correspond to the monoclonal antibody TRA-1-60 or TRA-1-81. One antibody corresponds to another antibody if both antibodies recognize the same or overlapping antigen binding sites as demonstrated by, for example, a binding inhibition assay commonly known to those in the art (*Antibodies: A Laboratory Manual;* Harlow & Lane, Cold Spring Harbor Laboratory, current edition). In still another embodiment, the hEG can also express the cell surface antigen SSEA-3. Depending upon the culture conditions, in still another embodiment, the hEG can differentiate into a variety of mature adult cell phenotypes that stain positively for particular biochemical markers and do not stain for other biochemical markers. Differentiated hEGs also exhibit, in still another embodiment, mature morphological features that enable one skilled in the art to distinguish them from non-differentiated hEGs.

In another embodiment, the invention provides a method to produce human "transplants" using hEG cells of the present invention. The term "transplants" is used to describe cells (or parts thereof), cell products, tissue, or cell culture products derived from hEG cells that are grafted into a human host. Specifically, a transplant is produced by manipulating hEGs, which exhibit a pluripotent embryonic germ cell phenotype, in vitro to produce hEG derived stem cells of restricted developmental lineage. By the term "restricted developmental lineage" is meant that the prospective fate of the stem cells derived from the hEG cell is reduced to a smaller number of possible histotypes after induction of differentiation. Methods of inducing in vitro differentiation of hEG cells such as using retinoic acid or by the removal of cell feeder layers or conditioned media are commonly known to those in the art. The resulting stem cells of restricted developmental lineage can be further manipulated to include exogenous genetic material known as a transgene. Provided that the cell expressing an hEG phenotype is genetically manipulated to include exogenous material, the resulting transplant can include exogenous material within some, but not all of its cells. Resulting transplant cell lines of restricted developmental lineage can be maintained or further manipulated as pure cell lines by techniques common to those in the art.

The term "transgenic" is used to describe an animal or any part thereof, including, but not restricted, to cells, cultures or tissues which includes exogenous genetic material within its cells. Cells of the invention can have DNA added to them and these cells can then be used in a manner similar to that for making a chimeric organism.

"Transgene" means any piece of DNA inserted by artifice into a cell that becomes part of the genome of the cell, cell line, tissue or organism (i.e., either stably integrated or as a stable extrachromosomal element) which develops from that cell. Such a transgene may include a gene which is partly or entirely heterologous (i.e., foreign) to the cell or organism to which the heterologous gene is introduced, or may represent a gene homologous to an endogenous gene of the organism. Included within this definition is a transgene created by the providing of an RNA sequence that is transcribed into DNA and then incorporated into the genome. The term "transgenic" as used herein additionally includes any organism or any part thereof, including, but not restricted, to cells, cell lines, cell cultures or tissues whose genome has been altered by in vitro manipulation or by any transgenic technology to induce a specific gene knockout. The term "gene knockout" as used herein, refers to the targeted disruption of a gene with complete loss of function achieved by any transgenic technology familiar to those in the art. In one embodiment, transgenic cells having gene knockouts are those in which the target gene has been rendered nonfunctional by an insertion targeted to the gene to be rendered nonfunctional by homologous recombination. As used herein, the term "transgenic" includes any transgenic technology familiar to those in the art which can produce an organism, cell, cell culture, cell line, tissue or embryo carrying an introduced transgene or one in which an endogenous gene has been rendered nonfunctional or "knocked out."

"Transfected" means a cell into which (or into an ancestor of which) has been introduced, by means of any recombinant nucleic acid techniques known to those in the art, a heterologous nucleic acid molecule. "Heterologous nucleic acid" refers to a nucleic acid sequence that either originates from another species or is modified from either its original form or the form primarily expressed in a cell.

The term "culture medium" means a suitable medium capable of supporting growth of hEG cells. Examples of suitable culture media useful in practicing the present invention are a variety of hEG growth media prepared with a base of Dulbecco's minimal essential media (DMEM) supplemented with 15% fetal calf serum, 2 mM glutamine, 1 mM sodium pyruvate, or glucose and phosphate free modified human tubal fluid media (HTF) supplemented with 15% fetal calf serum, 0.2 mM glutamine, 0.5 mM taurine, and 0.01 mM each of the following amino acids; asparagine, glycine, glutamic acid, cysteine, lysine, proline, serine, histidine, and aspartic acid (McKieman, S. M. Clayton, and B. Bavister, *Molecular Reproduction and Development* 42:188–199, 1995). An effective amount of factors are then added daily to either of these base solutions to prepare hEG growth media of the instant invention. The phrase "effective amount" as used herein is the amount of such described factor as to permit a beneficial effect on hEG growth and viability of hEG cells using judgement common to those in the art of cell culturing and by the teachings supplied herein.

One class of factors are ligands for receptors than can heterodimerize with the signal transduction molecule termed glycoprotein 130 (gp 130). For example, human recombinant leukemia inhibitory factor (LIF) at 1000U/ml or oncostatin-M at 10 U/ml, can be used (Koshimizu, U., et al., *Development* 122: 1235–1242, 1996).

A second class of factors are those which elevate intracellular cAMP levels. For example, one or more of the following factors can be used at the stated final concentration: forskolin at 10 μM, cholera toxin at 10 μM, isobutylmethylxanthine (IBMX) at 0.1 mM, dibutyrladenosine cyclic monophosphate (dbcAMP) at 1 mM (Dolci, S., M. Pesce, and M. De Felici, *Molecular Reproduction and Development* 35: 134–139, 1993; De Felici, M., S. Dolci, and M. Pesce, *Developmental Biology* 157: 277–280, 1993; Halaban, R., et al., 1993).

A third class of factors are growth factors. In one particular embodiment the growth factor is human recombinant basic fibroblast growth factor (bFGF) in the range of about 1–10 ng/ml. A fourth factor is growth media harvested from the culture of human embryonal carcinoma (EC) cells. In a particular embodiment, for example, human NTERA-2 EC cells (ATCC accession number CRL 1973) are grown to confluence in DMEM supplemented with 10% fetal calf serum or mouse ES cells are grown to confluence in DMEM supplemented with 15% fetal calf serum, 2 mM glutamine, 1000 U/ml LIF. Growth media is harvested daily over several days, passed through a 0.22 micron filter and frozen at −80° C. This EC or ES "conditioned" media is added to the hEG growth media in empirically determined amounts, as judged by the effect on hEG growth and viability.

The term "STO cell" refers to embryonic fibroblast mouse cells such as are commercially available and include those deposited as ATCC CRL 1503, and ATCC 56-X. After the hEG cells of the invention are isolated, they can be maintained by any method known in the art. Methods of growth and maintenance of cells are also well known in the art, (see Maniatis, et al., *Molecular Cloning: A Laboratory Manual,* Cold Spring Harbor Laboratory, Cold Spring Harbor, N.Y., current edition, incorporated herein by reference).

In one aspect of the invention, the pluripotent hEG cell lines offer a valuable paradigm for the immunohistological investigation of early human development by using monoclonal antibodies specific for cell surface glycolipids (Chiquoine, A. D., *Anat. Rec.,* 118: 135–146, 1954; Evans, M. J., and M. H. Kaufman, *Nature* 292: 154–156) and glycoproteins (Hogan, B. L. M., U.S. Pat. No. 5,453,357) of the cells of the present invention. These reagents are developed by immunization of mice with mouse and human teratocarcinoma cell lines, as well as mouse embryos. A number of monoclonal antibodies which bind to embryonic cell surface epitopes have been produced in this manner, and are important in the elucidation of glycosylation pathways during development. Monoclonal antibodies which bind to cell surface glycolipids and glycoproteins have been used to study human germ cell tumors (Labosky, P. A., D. P. Barlow, and B. L. M. Hogan, *Development* 120: 3197–3204, 1994; Matsui, Y., D., et al., *Nature* 353: 750–751, 1991) and other cancers (Resnick, J. L., et al., *Nature* 359: 550–551, 1992; Thomson, J. A., et al., *Proc. Natl. Aca. Sci. USA* 92: 7844–7848, 1992).

To generate human specific embryonic cell surface antibodies, BALB/c mice are immunized weekly with $10^6$ to $10^7$ hEG cells, and tail-bled weekly to test for reactivity to hEG cells. After reactive sera is detected, hybridomas are produced as described (Andrews, P., et al., *Hybridoma* 3: 347–361, 1984) or by standard methods. Resultant monoclonal antibodies are screened against a panel of human cell lines including EG and EC, as well as tissue sections from a variety of germ cell tumors and normal human tissues. Mouse ES, EG, and EC lines are also examined. Other methods of making antibody fragments are known in the art. (See for example, Harlow and Lane, *Antibodies: A Laboratory Manual,* Cold Spring Harbor Laboratory, New York (current edition), incorporated herein by reference). The term "antibody" as used in this invention includes intact molecules as well as fragments thereof, such as Fab, Fab', F(ab')$_2$, and Fv that can bind the epitopic determinant. As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

If needed, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See, e.g., Coligan, et al., *Current Protocols in Immunology,* Wiley Interscience, current edition, incorporated by reference).

"Purified antibody" means an antibody that is at least 60%, by weight, free from proteins and naturally-occurring organic molecules with which it is naturally associated. Preferably, the preparation is at least 75%, more preferably 90%, and most preferably at least 99%, by weight, antibody, e.g., an anti-SSEA-1 specific antibody. A purified antibody may be obtained, for example, by affinity chromatography using recombinantly-produced protein or conserved motif peptides and standard techniques. The invention can employ not only intact monoclonal or polyclonal antibodies, but also an immunologically-active antibody fragment, such as a Fab, Fab' or (Fab')$_2$ fragments, or a genetically engineered Fv fragment (Ladner et al., U.S. Pat. No. 4,946,788).

The methodology and cells of the present invention have a variety of different uses. The cells can be used to study human embryological development. For example, the cells of the invention which exhibit embryonic stem cell phenotype can be manipulated with detectably-labeled markers. The markers can then be inserted into blastocysts to observe distribution and cell lineages during development of the embryo.

"Detectably-labeled" refers to any means for marking and identifying the presence of a cell or part thereof, i.e., an oligonucleotide probe or primer, an antibody or fragment thereof, a protein or fragment thereof, a gene or fragment thereof, or a cDNA molecule. Methods for detectably-labeling cells or molecules are well known in the art and include, without limitation, radioactive labeling (e.g., with an isotope such as $^{32}$P or $^{35}$S) and nonradioactive labeling (e.g., chemiluminescent labeling, fluorescent labeling, enzymatic reaction products coded by genes, i.e., CAT).

Some additional advantages of using the cells of the invention which exhibit a pluripotent embryonic germ cell phenotype are as follows: A transgene of interest is introduced into an hEG cell or hEG cell line of the present invention by electroporation, calcium phosphate, microinjection, lipofection, retro- or other viral or microbial vector or other means and its integration and expression characterized in vitro. The effect of the introduced gene on the transformed hEG cell is then studied in vitro. The site in the hEG cell genome at which the introduced gene integrates can then be manipulated, for gene targeting and gene replacement (Thomas, K. R. and Capecci, M. R. *Cell* 51: 503–512, 1987).

Additionally, the hEG cells or cell lines of the invention are a source of RNA for the construction of early development and human pluripotent embryonic germ cell cDNA libraries. Gene expression during the early stages of human development, and in cells which retain pluripotency, has traditionally been difficult to study due to the scarcity of pertinent nucleic acid, molecules, cells and tissues. Using the techniques of the present invention, one of ordinary skill in the art can overcome these difficulties by generating stage specific human nucleic acid, molecules, cells, tissues and genetic material.

Pharmaceuticals, diagnostics, or antibodies, used in manufacturing or processing, are also produced using cells of the present invention. Exogenous foreign or homologous DNA is transferred to hEG cells by electroporation, calcium phosphate, microinjection, lipofection, retro- or other viral or microbial vector or other means. The hEG cells are screened for incorporation of this DNA, or are directly transferred to embryos to produce chimeras, or are used in nuclear transfer systems. These proteins or other molecules are harvested from resulting cell cultures for further purification. For example, human blood clotting factor IX may be produced for treatment of hemophilia.

Non-limiting examples of the following pharmaceutical, therapeutic, processing, manufacturing or compositional proteins that may be produced in this manner include: blood proteins (clotting factors VIII and IX, complement factors or components, hemoglobins or other blood proteins and the like); hormones (insulin, growth hormone, thyroid hormone, gonadotrophins, PMSG, trophic hormones, prolactin, oxytocin, dopamine, catecholamines and the like); growth factors (EGF, PDGF, NGF, IGF and the like); cytokines (interleukins, CSF, GMCSF, TNF, TGFα, TGFβ, and the like); enzymes (tissue plasminogen activator, streptokinase, cholesterol biosynthetic or degradative, digestive, steroidogenic, kinases, phosphodiesterases, methylases, de-methylases, dehydrogenases, cellulases, proteases, lipases, phospholipases, aromatase, cytochromes adenylate or guanylate cyclases and the like); hormone or other receptors (LDL, HDL, steroid, protein, peptide, lipid or prostaglandin and the like); binding proteins (steroid binding proteins, growth hormone or growth factor binding proteins and the like); immune system proteins (antibodies, SLA or MHC gene products); antigens (bacterial, parasitic, viral, allergens, and the like); translation or transcription factors, oncoproteins or proto-oncoproteins, milk proteins (caseins, lactalbumins, whey and the like); muscle proteins (myosin, tropomyosin, and the like).

The nucleotide sequence of the transgene may encode a precursor form of the protein ultimately harvested from the transgenic or transformed cells or cell cultures of the present invention. Preferably, expression of the transgene is inducible. Alternatively, cells may be screened by techniques well known to those of ordinary skill in the art to determine the expression of the transgene by using it as a probe for testing mRNA from cell lines.

Production of differentiated cells for replacement, repair or augmentation of damaged, nonfunctional, or impaired cells or tissues are another use and embodiment provided by the present invention. Exogenous foreign or homologous DNA is transferred to hEG cells by electroporation, calcium phosphate, microinjection, lipofection, retro- or other viral or microbial vector or other means. The hEG cells are screened for incorporation for this DNA or used in nuclear transfer systems. These cells and/or tissues are harvested from cell cultures, or resulting cell lines for use in repairing or augmenting a defect. For example, cells, cell products, tissues or the products of cell cultures may be used in treating subjects having Parkinson's disease or subjects who have had a heart attack or spinal cord injury.

Cells, tissues or organs with exogenous major histocompatibility or other foreign or endogenous antigens and/or genes that will decrease rejection by the host organism of these transplanted materials are produced by means of the present invention. Exogenous foreign or homologous DNA is transferred to hEG cell phenotype by electroporation, exposure to calcium phosphate, microinjection, lipofection, retro- or other viral or microbial vector, or other means. The hEG cells are screened for incorporation of this DNA or expression of antigens, used in nuclear transfer systems, or grown in vitro culture. Molecules, proteins, cells, tissues, organs, fluids, or cell products are harvested from cells, cell lines, cell cultures for xenotransplantation. In this manner, humanized molecules, proteins, cells, cell products, cell constituents, tissues, organs or fluids are possible.

In another embodiment, the invention provides methods to generate cells and tissues from hEG lines for human transplantation. Towards that end, it may be necessary to eliminate or reduce cell-surface marker molecules on donor transplantation cells or tissues that induce organ graft rejection. The present invention encompasses all such modifications that reduce or eliminate organ graft rejection when employing cells, cell lines (or any parts or derivatives thereof) from the present invention. These molecules, termed HLA antigens in humans, comprise MHC class I and II membrane glycoproteins. For non-hematopoietic cells and tissues, elimination or reduction of MHC class I molecules is accomplished by targeted knockout of the human $\beta_2$-microglobulin gene, as has been accomplished with mouse ES cells (Zijlstra, M., et al, *Nature* 342: 435–438, 1989). Non-hematopoietic cells do not normally produce MHC class II molecules. For hematopoietic cells, the presence of MHC class II glycoproteins may be reduced or eliminated by targeted knockout of the HLA-DP, -DQ, and -DR loci, which are analogous to knockouts of the E and A loci in mouse ES cells (Cosgrove, D., et al, *Cell* 66:1051–1066, 1991).

EXAMPLES

All references cited herein are hereby incorporated by reference in their entirety. The following examples are intended to illustrate but not limit the invention. While they are typical of those that might be used, other procedures known to those skilled in the art may alternatively be used.

EXAMPLE 1
Collection and Preparation of Human Primordial Embryonic Germ Cells

Gonadal anlagen or genital ridges with mesenteries were dissected from 8–11 week LMP (last menstrual period) human aborted fetal material. The genital ridges were placed into approximately 0.5 ml phosphate buffered saline solution (PBS 0.21 g/L $KH_2PO_4$; 9 g/L NaCL; 0.726 g/L $Na_2HPO_4 7H_2O$), and were cut into small (less than 1 $mm^3$) chunks. The chunks were then further minced with a fine forceps. The tissues were then transferred to a 15 ml polypropylene conical tube, and allowed to settle. A majority of the PBS was then carefully removed, and 1 ml 0.05% trypsin-0.53 mM Sodium EDTA solution (BRL) was added to the tube. The tissue was then repeatedly pipetted through a 100 ul pipet tip to further disaggregate the cells. The tubes were subsequently stored on ice for less than 1 hour.

The tissue and cell suspension was incubated at 37° C. for approximately 5 min., then 15 ml EG growth media (D-MEM, 4500 mg/L D-glucose, 2200 mg/L mM Sodium bicarbonate); 15% ES qualified fetal calf serum (BRL); 2 mM glutamine (BRL); 1 mM Sodium Pyruvate (BRL); 1000 U/ml human recombinant leukemia inhibitory factor (LIF, Genzyme); 1 ng/ml human recombinant basic fibroblast growth factor (bFGF, Genzyme); 10 uM Forskolin in 10% DMSO was added. The tissue and cell suspension was then spun at 1000 rpm for 5 min. The EG growth media was carefully removed, and the cells were resuspended in 3.2 ml EG growth media.

Approximately 0.2 ml of the cell suspension was added to each of 16 wells of a 96-well tissue culture plate previously prepared with a sub confluent layer of STO mouse fibroblasts that had been cultured for 3 days in hEG growth media that did not contain LIF, bFGF or Forskolin, then irradiated with 5000 rad of gamma irradiation.

The human PGC cells and STO mouse fibroblasts were cultured for 7–10 days in hEG growth media at 37° C. with 5% $CO_2$ at 90% humidity. Growth media was freshly prepared and replaced daily.

The cells were trypsinized as described here, and each well was passaged to 1 well of a 24-well culture dish previously prepared with irradiated STO mouse fibroblasts (9/10 cells) and to 1 well of a 96-well tissue culture plate previously prepared with irradiated STO mouse fibroblasts (1/10 cells).

The cells were cultured for 3 days with daily replacement of growth media. On the 13th day of culture (3 days after subculture), a subset of cells growing on the 96-well culture dish were fixed and stained for the presence of alkaline phosphatase by using a commercially available diagnostic kit (Sigma Chemicals, product number 86-R). The cells are washed 2 times with phosphate buffered saline (PBS) then fixed for 30 seconds in Citrate-Acetone-Formaldehyde solution. Fixed cells are then incubated in the dark for 15 min. in Alkaline-dye mixture. The cells are then rinsed with deionized water for 2 min. and allowed to dry. Alkaline phosphatase positive PGC and EG cells stain red, while cells that lack alkaline phosphatase activity, such as STO cells, remain clear.

Cells growing on the 24-well plate were passaged four times to expand cell numbers, and multiple frozen stocks from each passage were prepared. Cells were photographed throughout the initial 13 days of culture using phase contrast microscopy and selected cells were processed for alkaline phosphatase staining as described herein.

EXAMPLE 2
Passage of Pluripotent Cells hEG growth media was replaced daily, and the cells were grown at 37° C., 90% relative humidity, 5% $CO_2$ for 10–14 days. At this time, the cells were trypsinized and subcultured to freshly prepared 96-well or 24-well plates with irradiated feeder layer or matrix. A subpopulation of these cells were fixed and stained for alkaline phosphatase activity. These cells were passaged at least 4 times over a 40 day period, with continued demonstration of alkaline phosphatase activity as demonstrated by positive staining.

After 1 to 3 passages (7 to 30 days) some cells in the human PGC culture change from isolated and solitary human PGCs, readily identified only by alkaline phosphatase staining or antibody detection, to large multicellular and compact clusters. These clusters can be recognized by light microscopy and resemble early passage mouse ES and EG cells. Like the solitary human PGC cultures, the multicellular cluster human EG cells can be characterized with respect to alkaline phosphatase activity, presence of cell surface antigens, and ability to form teratocarcinomas in SCID mice. The multicellular clusters are isolated from the rest of the culture using a cloning cylinder, expanded through repeated passage, then characterized as separate cell lines.

To test for teratocarcinoma formation in SCID mice, a pellet consisting of approximately 500,000 hEG cells is injected into the rear leg muscle, testis, or kidney capsule of 8–15 week old SCID mice. After 8–20 weeks of development, the resulting tumors are fixed in 4% paraformaldehyde and embedded in paraffin. Tissue sections are examined using standard histological staining techniques and immunohistochemical detection of cell surface antigens and other epitopes as described herein.

EXAMPLE 3
Testing Harvested Cells for Morphology and Alkaline Phosphate Activity As previously described, in a preferred embodiment primordial germ cells (PGCs) are harvested from nascent gonadal ridges since their early developmental age inhibits subsequent differentiation and loss of pluripotency.

To ascertain that harvested cells are of an appropriate developmental age, harvested cells were tested for morphological criteria used to identify primordial germ cells that are pluripotent (DeFelici and McLaren, *Exp. Cell.* 142: 476–482, 1982). To further substantiate pluripotency a sample of the extracted cells are subsequently tested for alkaline phosphatase (AP) activity. Markers for pluripotent cells are often useful to identify stem cells in culture. hEG cells typically manifest alkaline phosphatase (AP) activity and AP positive cells are typically pluripotent. AP activity is rapidly lost with differentiation of hEG cells in vitro. AP expression has been demonstrated in ES and ES-like cells in the mouse (Wobus et al., *Exp. Cell* 152: 212–219, 1984; Pease et al., *Dev. Bio.* 141: 344–352, 1990), rat (Ouhibi et al., *Mol. Repro. Dev.* 40: 311–324, 1995), pig (Talbot et al., *Mol. Repro. Dev.* 36: 139–147, 1993b) and cow (Talbot et al., *Mol. Repro. Dev.* 42: 35–52, 1995). AP activity has also been detected in murine PGCs (Chiquoine, *Anat. Rec.* 118: 135–146, 1954), murine EG cells (Matsui et al., *Cell* 70: 841–847, 1992; Resnick et al., *Nature* 359: 550–551, 1992) and cultured avian embryonic cells from chickens (Pain et al., *Dev.* 122:1996). In conjunction with morphological evaluation of the hEG cell colony, AP expression is a convenient marker to identify pluripotent embryonic germ cells in culture.

Cell samples taken from hEG cell lines cultured from 8–11 week LMP gonadal ridges (generated as in Example 2) were assessed, using light microscopy, for the presence of morphological criteria indicative of putative hEGs. The hEGs first appeared either as round cells or round cells with two or more extended pseudopodia when visualized after staining for alkaline phosphatase (AP) activity. After 1–4 weeks in culture, multicellular colonies of hEGs developed. First, 10 to 100 individual cells formed a loosely associated aggregation. In subsequent passages, some colonies became larger and appeared to be comprised of many cell layers. The individual cells of these colonies appeared small and more tightly associated. hEG cultures are maintained for greater than 3 months by passage every 7–10 days onto fresh irradiated mouse STO fibroblasts. After approximately 2 months, some hEGs formed colonies with larger diameter but fewer cell layers. The cells demonstrated a tightly clustered and rapidly growing morphology reminiscent of early passage mouse ES and EG cultures.

Subsequently, cells were tested for alkaline phosphatase activity by fixing them in 80% ethanol (Buehr and McLaren, *Meth. Enzymol.* 225: 58–77, 1993) and staining them employing a protocol from an AP cytochemistry kit (Sigma Chemical Co., St. Louis, Mo.). The results indicated that AP activity was consistently expressed in hEGs, and in primary cultures and subcultures of hEG cells. The cells demonstrated strong and convincing histological staining for alkaline phosphatase. Surrounding STO mouse fibroblasts did not stain for alkaline phosphatase. Therefore, cells testing positive for both morphological criteria and AP activity are indicative of ES-like cells and these cells typically make up 50–90% of all harvested cells.

EXAMPLE 4
Pluripotency of hEG Determined by Antibody Staining

Other indicators of pluripotency can also be investigated. These include, but are not limited to, the presence of stage specific embryonic antigens such as SSEA-1 (Solter, D. and B. Knowles, *Proc. Natl. Acad. Sci. USA* 75: 5565–5569, 1978), SSEA-3, SSEA-4 (Kannagi, R., et al., *Embo J.* 2: 2355–2361, 1983) and epitopes recognized by the antibodies TRA-1-60 and TRA-1-82 (Andrews, P., et al., *Hybridoma* 3: 347–361, 1984) and the ability of these cells to form teratocarcinomas or teratomas when injected into immuno-compromised (SCID) mice.

hEG cultures grown on plastic chamber slides were stained with 5 monoclonal antibodies to embryonic cell surface antigens. Cells were rinsed 2 times with phosphate buffered saline (PBS) then fixed in 3% paraformaldehyde for 15 minutes at room temperature. The cells were washed two times in PBS, then incubated in a 1:5 to 1:25 dilution (in PBS) of each of the following monoclonal antibodies for 1 hour at room temperature: TRA-1-81 and TRA-1-60 (supplied by Dr. Peter Andrews, Sheffield, UK); MC-480 (anti-SSEA-1), MC-631 (anti-SSEA-3), and MC-813-70 (anti-SSEA-4) (anti-SSEA antibodies were supplied by the Developmental Studies Hybridoma Bank, Iowa City, Iowa).

The cells were subsequently washed times two in PBS. Biotinylated anti-mouse immunoglobulin secondary antibody, and horseradish peroxidase-conjugated strepavidin (BioGenex, San Ramon, Calif.) were used as recommended by the manufacturer.

Antibodies to SSEA-1 and -4 antigens and TRA-1-60, and -81 reacted strongly to the hEG cells, while the antibody to SSEA-3 reacted weakly. hEG cells also reacted positively for AP.

EXAMPLE 5
Cultured hEG Cells Display Normal Karyotypes

Due to their rapid proliferation in culture established ES cells have been reported to contain abnormal karyotypes (Abbondanzo, S. J. et al., *Meth. Enzymol.* 225: 803–823, 1993). Additionally, repeated freezing and thawing of cyropreserved ES cells may elevate the risk of inducing chromosomal abnormalities. To maximize the potential of successful germ-line genetic manipulation (e.g., gene targeting) when using hEG cells, hEG cell lines exhibiting normal diploid karyotypes are preferred. To determine whether human hEG cell lines exhibited normal karyotype, hEG cells which were cultured as described herein were tested. Approximately 10–20 metaphase stage karyotypes from each hEG cell line were tested by examining the cell's chromosomes for both structural and numerical abnormalities. Two hEG cultures were karyotyped and were normal 46,XY and 46,XX, respectively. Colonies from these cultures were isolated and expanded two separate times to generate hEG lines.

Cells were placed in 4-well culture dishes and cultured overnight in hEG culture medium containing 0.02 ug/ml colcemid (GIBCO BRL) at 39° C. in 5% $CO_2$, 95% air. Cells were subsequently washed in PBS, treated with 0.25% trypsin-EDTA for 10–15 minutes at 39° C., removed and centrifuged for five minutes at 800×gravity. Cells were fixed for five minutes in cold Carnoy's fixative (3:1 volume of absolute methanol to glacial acetic acid), washed in PBS, centrifuged as above, and resuspended in 0.5 ml of Carnoy's fixative. A pipette drop of the resulting cell suspension was transferred onto microscopic slides that were prewashed with Carnoy's fixative. Slides were air dried, Giemsa stained (GIBCO, BRL) and rinsed with tap water. After a second drying, slides were cover slipped and viewed under oil immersion using light microscopy at 400X magnification.

All hEG cell lines examined had a normal complement of human chromosomes (i.e., 44 autosomes and 2 sex chromosomes). Additionally, no breaks, deletions, additions or other abnormalities in the shape or number of chromosomes were observed. Additionally, hEG cells that survived cryopreservation and subsequent culturing also displayed no chromosomal abnormalities or overt changes in phenotypic characteristics. Among isolated hEG cell lines, no obvious differences were observed in morphology, proliferation and AP activity. The hEG cells expressed AP activity, as consistently observed in EGs and embryonic germ cells in primary culture and subcultures but not in STO feeder cells. When the hEG cells differentiated in vitro, they rapidly lost AP activity. After 8 to 12 passages, all 4 isolated hEG cell lines had a normal human complement of 46 chromosomes (44 autosomes and 2 sex chromosomes). No obvious abnormalities, additions or deletions are found in chromosomes from isolated hEG cells as described above.

TABLE 1

Characteristics of human EG cell lines

| hEG Cell Line | Collected From | Karyotype (2N) | No. of Current Passage |
|---|---|---|---|
| KH | 9 week LMP | 46, XX | 20 |
| GU | 11 week LMP | 46, XY | 30 |

EXAMPLE 6
Use of Human Pluripotent Embryonic Germ Cells (hEG) to Generate a cDNA Library hEG cells of the present invention are a plentiful source of pluripotent cell mRNA to create cDNA libraries and templates for polymerase chain reaction based experimentation.

hEG lines were cultured in the presence of irradiated mouse STO fibroblasts. Several steps were taken to eliminate STO cells and STO cDNA. Approximately $10^6$ hEG cells growing on irradiated STO fibroblasts were trypsinized and resuspended in hEG media The resuspended cells were plated on a tissue culture dish and allowed to sit for 1 hour. During this time, STO fibroblasts adhere while hEG cells do not. Unattached cells were gently removed and the plating procedure was repeated twice. This series of preferential bindings effectively removes 50–90% of STO cells. Remaining hEG cells were spun at 1000 rpm for 5 minutes, and the pellet was used to generate RNA, mRNA and then cDNA. The cDNA was subjected to several rounds of subtraction using STO cell RNA, by a commonly described methodology (Maniatis, et al., *Molecular Cloning: A Laboratory Manual,* Cold Spring Harbor Laboratory, Cold Spring Harbor, N.Y., current edition, incorporated herein by reference in its entirety). This removed STO and fibroblast cDNAs. The remaining cDNA was enriched for the human cDNAs unique to pluripotent cells. Many cDNA library screenings can be employed on this cDNA library, as well as other DNA subtractions commonly known to those in the art (Maniatis, et al., *Molecular Cloning: A Laboratory Manual,* Cold Spring Harbor Laboratory, Cold Spring Harbor, N.Y., current edition, incorporated herein by reference, in its entirety).

Although the invention has been described with reference to the presently preferred embodiment, it should be understood that various modifications can be made without departing from the spirit of the invention. Accordingly, the invention is limited only by the following claims.

What is claimed is:

1. Human pluripotential embryonic germ cells, wherein the cells exhibit the following culture characteristics during maintenance:
   (a) dependence on a ligand which binds to a receptor which can heterodimerize with glycoprotein 130 (gp 130); and
   (b) dependence on a growth factor.

2. The cells of claim 1, wherein the growth factor is basic fibroblast growth factor (bFGF).

3. The cells of claim 1, wherein the cells are alkaline phosphatase positive.

4. The cells of claim 1, wherein the cells express cell surface antigen SSEA-4, and cell surface antigens which bind with antibodies having the binding specificity of monoclonal antibodies TRA-1-60 and TRA-1-81.

5. The cells of claim 4, wherein the cells express cell surface antigen SSEA-3.

6. The cells of claim 1, wherein the ligand is oncostatin-M.

7. The cells of claim 1, wherein the ligand is leukemia inhibitory factor (LIF).

8. The cells of claim 1, wherein the cells are derived from gonadal ridge tissue.

9. The cells of claim 8, wherein the gonadal ridge tissue is 3 to 13 weeks post-fertilization.

10. The cells of claim 8, wherein the gonadal ridge tissue is 8 to 11 weeks after the last menstrual period.

11. The cells of claim 1, wherein the cells are SSEA-1 positive.

12. The cells of claim 1, wherein the culture characteristics further comprise a factor which elevates intracellular cAMP.

13. The cells of claim 12, wherein the factor which elevates intracellular cAMP is selected from the group consisting of forskolin, cholera toxin, isobutylmethylxanthine and dibutyladenosine cyclic monophosphate.

14. The cells of claim 12, wherein the factor which elevates intracellular cAMP is forskolin.

15. The cells of claim 1, wherein the cells retain the ability to proliferate after being cryopreserved.

* * * * *